US008575289B1

(12) United States Patent
Harry-O'kuru et al.

(10) Patent No.: US 8,575,289 B1
(45) Date of Patent: Nov. 5, 2013

(54) ELASTOMER PRODUCT FROM EPOXIDIZED VEGETABLE OIL AND GLIADIN

(75) Inventors: Rogers E. Harry-O'kuru, Peoria, IL (US); Abdellatif Abdelhakim Mohamed, Riyadh (SA); Sherald H. Gordon, Peoria, IL (US); Jingyuan Xu, Dunlap, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 101 days.

(21) Appl. No.: 13/178,676

(22) Filed: Jul. 8, 2011

(51) Int. Cl.
*C07K 1/107* (2006.01)
*A61K 9/16* (2006.01)
*C08L 89/00* (2006.01)

(52) U.S. Cl.
USPC .......................... 527/200; 527/202; 527/204

(58) Field of Classification Search
USPC ........................................ 527/200, 202, 204
See application file for complete search history.

(56) References Cited

U.S. PATENT DOCUMENTS

| | | | | |
|---|---|---|---|---|
| 4,128,539 | A | * | 12/1978 | Onizawa .................... 525/187 |
| 4,886,893 | A | * | 12/1989 | Meffert et al. ............. 549/562 |
| 2004/0230009 | A1 | * | 11/2004 | Wilkes et al. ............. 525/327.3 |
| 2004/0258635 | A1 | * | 12/2004 | Harry-O'kuru ............. 424/59 |

OTHER PUBLICATIONS

Harry-O'Kura et al., A Facile Synthesis of Aminohydryoxy Triglycerides from New Crop Oils, 2005, JAOCS, vol. 82, No. 3, pp. 207-212.*
Harry-O'Kuru, R.E., et al., "A Facile Synthesis of Aminohydroxy Triglycerides from New Crop Oils", JAOCS, vol. 82, No. 3, 2005, pp. 207-212.

* cited by examiner

*Primary Examiner* — James J Seidleck
*Assistant Examiner* — Peter A Salamon
(74) *Attorney, Agent, or Firm* — John Fado; Albert Y. Tsui; Lesley Shaw

(57) ABSTRACT

Disclosed is a bio-based and environmentally friendly elastomer product from renewable agricultural substrates. Specifically, glutamine and arginine residues of gliadin are used as synthons to produce novel elastomeric product from the reaction of the oxirane groups of epoxidized vegetable oils under neat reaction conditions with the primary amide functionalities of glutamine and arginine to give the corresponding amidohyroxy gliadinyl triglycerides.

11 Claims, 9 Drawing Sheets

MKTFLILALLAIVATTATTAVRVPVPQLQPQNPSQQQPQ
EQVPLVQQQQFLGQQQPFPPQQPYPQPQPFPSQQPYLQLQ
PFLQPQLPYSQPQPFRPQQPYPQPQPQYSQPQQPISQQQQ
QQQQQQQQQQQQQQQIIQQILQQQLIPCMDVVLQQHNIV
HGKSQVLQQSTYQLLQELCCQHLWQIPEQSQCQAIHNVVH
AIILHQQQKQQQQPSSQVSFQQPLQQYPLGQGSFRPSQQ
NPQAQGSVQPQQLPQFEEIRNLARK

SEQ ID NO. 1

FIG. 2

ELASTOMER PRODUCT FROM EPOXIDIZED VEGETABLE OIL AND GLIADIN

FIELD OF INVENTION

This invention relates to an elastomer product resulting from the amidolysis of oxirane groups contained in vegetable oils with the primary amide groups of glutamine or arginine found in the glycoprotein gliadin under neat conditions.

BACKGROUND OF INVENTION

Various approaches have been taken to develop degradable or biodegradable synthetic plastic materials. These approaches include photodegradation where a polymer such as polyethylene is synthesized incorporating functional groupings such as a carbonyl that could undergo photolysis in the environment during disposal. Another approach is to produce polyesters and polyamides that are truly biodegrade. Such examples include poly caprolactams/polycaprolactones (Potts, et al., *Am. Chem. Soc., Polymer Preprints*, 1972, 13(2), 629), polyhydroxy butyrate (PHBs), polyhydroxybutyrate-co-valerates (Holmes, P. A., *Phys. Technol.* 1985, 16, 32-36), and poly lactides.

More recent approaches include plastics such as glycidyl monomers such as Bisphenol A diglycidyl ether or Bisphenol A propoxylate diglycidyl ethers to form BPA-polycarbonates formed in whole or in part by BPA. However, the by-product contaminants from the manufacturing of bisphenols is problematic and produces various contaminants. For example, U.S. Pat. No. 6,133,486. Additionally, BPA polymetric products may present a problem as the BPA is known to be an endocrine disruptor. As such, BPA has been banned in Canada and EU in infant related items. Hence, there is a need to further develop a reaction process that preferably utilizes two completely renewable materials to generate novel elastomeric protein derivatives at moderate temperatures that could be used as stable environmentally friendly materials. Additionally, this reaction process would preferably not produce by-product contaminants.

BRIEF SUMMARY OF THE INVENTION

Disclosed herein is an elastomer composition comprising the reaction product of an epoxidized vegetable oil triglyceride having 3 to 5 oxirane moieties per triglyceride unit substituted with one or more of the glutamine or arginine moieties found in gliadin, wherein the reaction product forms an elastomer. In one embodiment of the invention, the epoxidized vegetable oil triglyceride is epoxidized soybean oil. In another embodiment of the invention, the epoxidized vegetable oil triglyceride is epoxidized milkweed oil. In yet another embodiment of the invention, the epoxidized vegetable oil triglyceride is epoxidized salicornia oil.

Also disclosed herein is a method for making an elastomer from a vegetable oil, the method comprising the steps of epoxidizing a vegetable oil with a peroxide to form an epoxidized vegetable oil, reacting said epoxidized vegetable oil having at least 3 oxirane moieties with one or more of the glutamine or arginine moieties found in gliadin, wherein an elastomer product is formed. In various embodiments of the inventions, either salicornia oil, milkweeds oil, or soybean oil is used.

BRIEF DESCRIPTION OF THE DRAWINGS

The present invention may best be understood from the following detailed descriptions of the embodiments of the invention illustrated in the drawings, wherein:

FIG. 2 is a segment of the proposed structure sequence of gliadin.

BRIEF DESCRIPTION OF THE SEQUENCE LISTING

Figure 1:
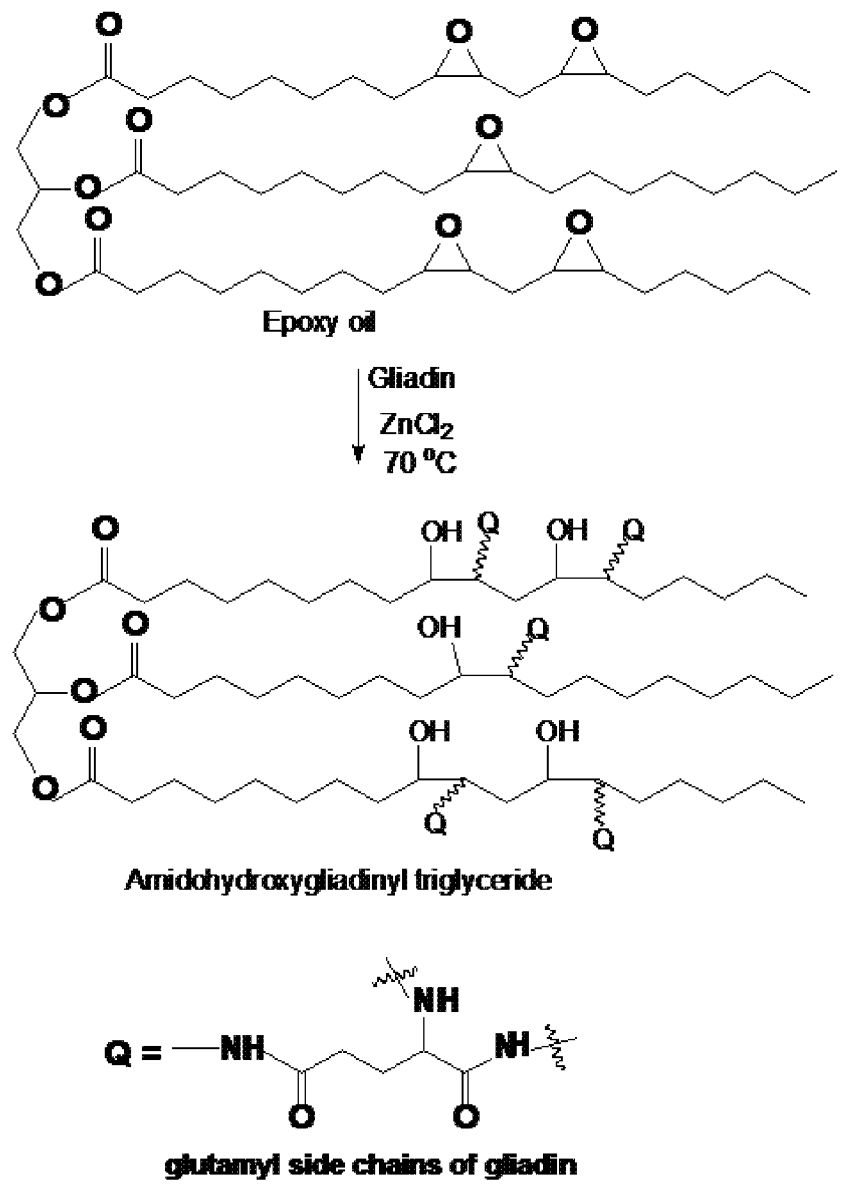
FIG. 1 depicts a scheme for the formation of amidohydroxygliadinyl triglycerides.
Figure 3:
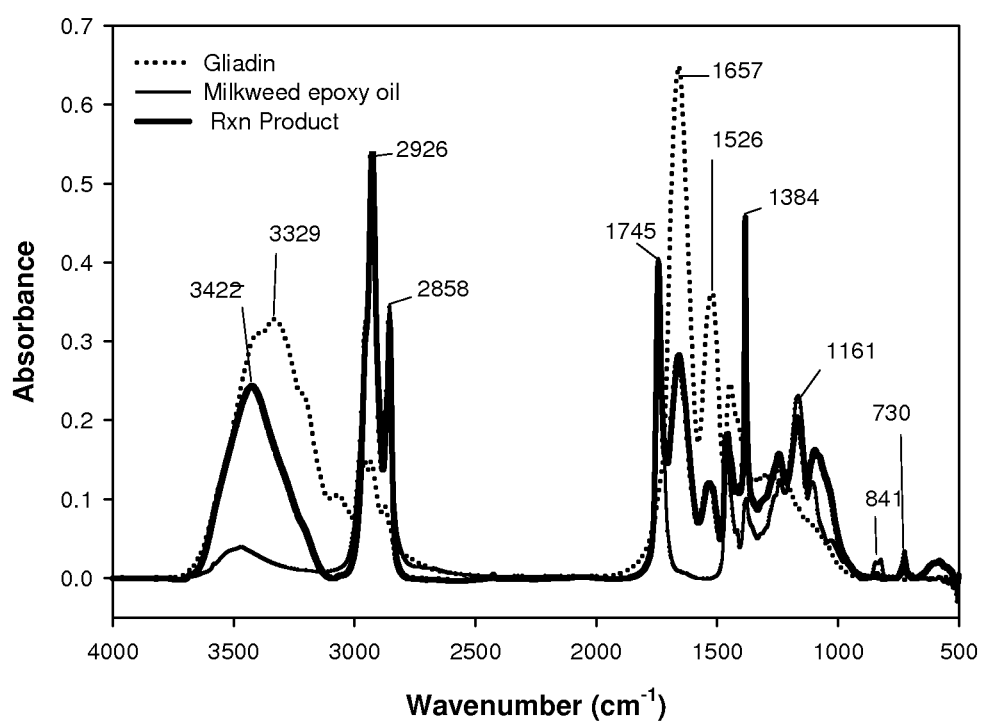
FIG. 3 is the FTIR spectra of gliadin, epoxidized milkweed oil, and their reaction product (milkglyde) in accordance with the scheme of FIG. 1.
Figure 4:
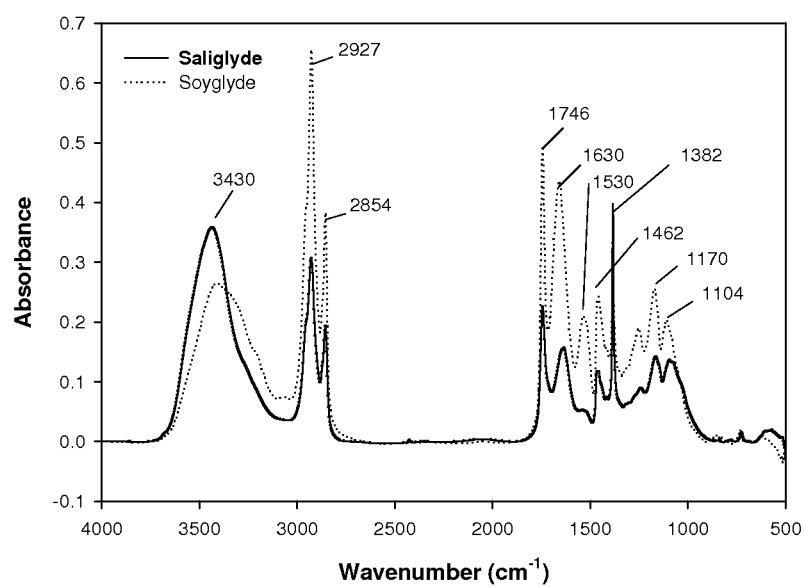
FIG. 4 is the FTIR spectra of the reaction products of epoxidized salicornia oil with gliadin (saliglyde) and reaction product of epoxidized soybean oil with gliadin (soyglyde) in accordance with the scheme of FIG. 1.
Figure 5:
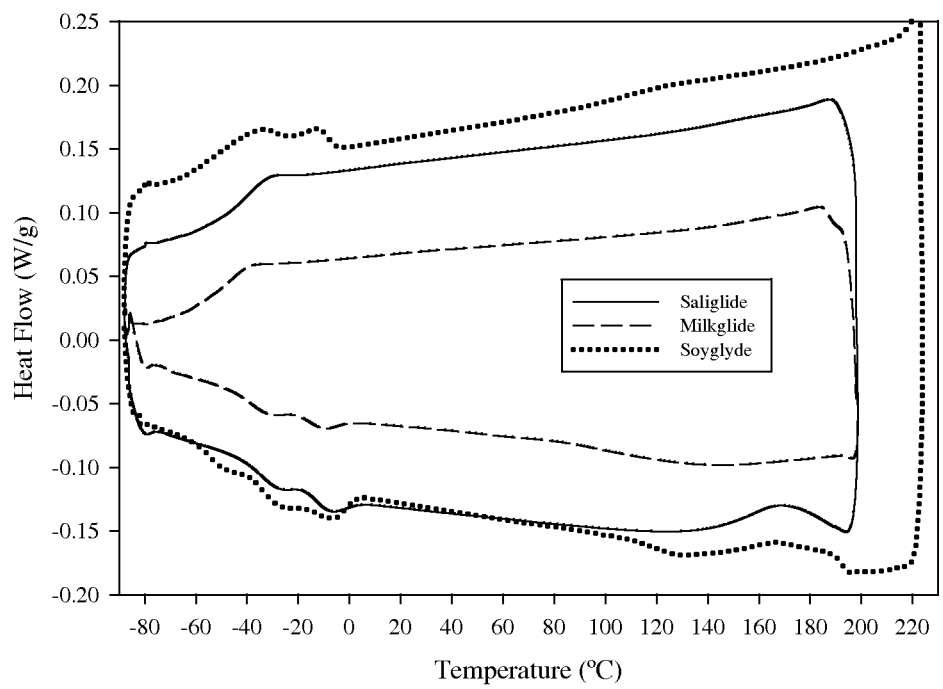
FIG. 5 is a differential scanning calorimetry thermogram of the reaction products of epoxidized salicornia oil with gliadin (saliglyde), epoxidized milkweed oil with gliadin (milkglyde), and epoxidized soybean oil with gliadin (soyglyde).

SEQ ID NO 1 is the amino acid sequence of proposed segment of gliadin. SEQ ID NO 2 is the amino acid sequence of a gliadin fragment.

DETAILED DESCRIPTION OF THE INVENTION

Definitions

As used in the specification and claims, the singular form "a", "an" and "the" include plural references unless the context clearly dictates otherwise.

One component of the reaction mixture is a vegetable oil. Examples of suitable vegetable oils include but are not limited to soybean oil, safflower oil, linseed oil, corn oil, sunflower oil, olive oil, canola oil, sesame oil, cottonseed oil, palm oil, rapeseed oil, tung oil, fish oil, peanut oil, cuphea oil, milkweed oil, salicornia oil and combinations thereof. Natural vegetable oils may be used, and also useful are partially hydrogenated vegetable oils and genetically modified vegetable oils, including high oleic safflower oil, high oleic soybean oil, high oleic peanut oil, high oleic sunflower oil, and high erucic rapeseed oil (crambe oil).

Epoxidation of vegetable oils may be carried out as described by Qureshi et al. [*Polymer Science and Technology*, Vol. 17, Plenum Press, p. 250] or by any other method as known in the art. For example, the epoxidation may be carried out by reaction of the milkweed oil with formic acid and hydrogen peroxide at an elevated temperature on the order of 75° C. The degree of epoxidation should be such that there are at least 3, and preferably at 4, or even 5, oxirane rings per triglyceride molecule. Typically, the epoxidation is carried to completion.

As used herein, "epoxidized vegetable oil" refers to a non-naturally occurring epoxy oil prepared by treating a vegetable oil so as to modify the chemical structure of the molecule to fully epoxidize the double bonds present in the vegetable oil.

Another component of the reaction mixture is gliadin. Gliadin is a single-chained protein having an average molecular weight of about 30,000-40,000, with an isoelectric point of pH 4.0-5.0. The gliadins comprise a multigene family and have been divided into four groups, called alpha-, beta-, gamma-, and omega-gliadins, based on their electrophoretic mobility at low pH. The amino acid compositions of the alpha-, beta-, and gamma-gliadins are similar to each other and to that of the whole gliadin fraction (Tatham et al., 1990, J. Biochem, 270(2):313-318). The omega-gliadins contain little or no cysteine or methionine and only small amounts of basic amino acids. All gliadins are monomers with either no disulphide bonds (omega-gliadins) or intrachain disulphide bonds (alpha-, beta-, and gamma-gliadins). Gliadin proteins are extremely sticky when hydrated and have little or no resistance to extension. The gliadin used in conjunction with the invention disclosed herein may be alpha, beta, gamma or omega gliadin or combinations thereof.

The synthons or reactive segments of gliadin in the reaction with epoxidized vegetable oils are chiefly the glutamine side chains together with the adjourning arginine side chains residues found in gliadin as shown in the proposed structure of gliadin in SEQ ID NO 1 (Cornell, H. J., et al., 1982. *Clinica Chimica Acta.,* 123:311-319. Cornell, H., et al., 1992, *Clinica Chimica Acta.,* 213:37-50, disclosed using a peptic-tryptic-pancreatinic digestion of gliadin isolated, inter alia, a fraction shown to have the sequence RPQQPYPQPQPQ (SEQ ID NO 2). This fraction which is part of the protein sequence of gliadin was known to be toxic to persons with coeliac disease. This invention on the other hand taps the potential of the natural toxicant in the formation of a useful elastomeric material.

Typically, an additional acid component will also be present in the reaction mixture. Examples of suitable additional acids include sulfuric acid, toluenesulfonic acid, trifluoroacetic acid, fluoroboric acid, Lewis acids, acidic clays, or acidic ion exchange resins.

Disclosed herein is a reaction of gliadin with the oxirane groups of epoxidized vegetable oil. Specifically, the reaction is an amidolysis of the oxirane units resulting in the gliadinyl amidohyroxy triglycerides. Depending on the epoxidized vegetable oil used, the resulting elastomeric product has been named by based on the starting vegetable oil. For example, if the reaction is between epoxidized salicornia oil and gliadin, the elastomeric product is named as "saliglyde". If the reaction is between epoxidized milkweed oil and gliadin, the elastomeric product is named "milkglyde". When the reaction is between epoxidized soybean oil and gliadin, the elastomeric product is named "soyglyde".

The physical property of the elastomeric product can be changed by changing the ratio of epoxidized oil to protein. A stoichiometric ratio of oxirane to protein for milkglyde was 69:31 in the reaction which resulted in an elastomeric product which exhibited higher strength as a solid. When a 19:6 ratio of epoxide to protein was used a pourable fluid elastomer reaction product was obtained. One having skill in the chemical arts would adjust the stoichiometric ratio of oxirane to protein to either form a solid or fluid elastomer product upon reading the disclosure herein.

One having skill in the chemical arts would adjust the stoichiometric ratio of oxirane to protein to either form a solid or fluid elastomer product upon reading the disclosure herein. The resulting elastomer is contemplated to be used a rubber substitute given its viscoelastic solid properties. Additionally it is contemplated that the elastomer would be amenable to additives such as plasticizers to increase flexibility or durability of the elastomer.

A polymer composite can be produced by blending this elastomer with additives or fillers. The properties of the composite are expectedly manipulable by adjusting additives. The fillers used can be in-organics such as glass fibers and flakes; organics such as carbon black and carbon fibers; as well as natural polymers such as cellulose fibers and starch. The size of the fillers could be in the range of micro to nano meters. To improve molding processing, plasticizers such as glycerol can be added.

Because the primary amide (O=C—NH$_2$) functional groups of glutamine and arginine are not avid nucleophiles, the reaction with epoxidized triglycerides is catalyzed by the presence of a Lewis acid such as ZnCl$_2$ by activating the oxirane carbons toward amidolysis by coordination to the epoxy oxygen. Other methods to activate the tertiary epoxy carbons through electron mobilization to the oxygen atom with other Lewis acids such as AlCl$_3$, CeCl$_3$, TiCl$_4$, or ZrCl$_4$.

Hereinafter, the present invention is explained in detail with reference to the following examples. The examples, however, should not in any sense be interpreted as limiting the scope of the present invention.

Example 1

Milkglyde

Synthesis of Milkweed Epoxy triglyceride

In a typical process reprocessed milkweed oil 582.0 g (673.76 mmol, iodine value, IV=111.4) were placed in a 1 L 3-necked jacketed flask equipped with a mechanical stirrer and heated to 45.5° C. Formic acid (96%, 39.7 g, 0.3 equiv/mol of C=C) was added and the mixture stirred to homogeneity. Hydrogen peroxide (50%, 320 mL, 5.65 mol) was then added slowly (i.e. dropwise). At the end of hydrogen peroxide addition the temperature was raised to 70° C. and vigorous stirring was continued for 7 h when a sample of the reaction mixture showed complete absence of the vinylic protons of the starting material. The heat source was then removed, the reaction mixture allowed to cool to near room temperature and transferred to a separatory funnel with ethyl acetate as diluent. The material was washed with saturated NaCl (300 mL×4) followed by saturated Na$_2$CO$_3$ (40 mL) in more NaCl solution. The washes were discarded. When pH 7.5 was reached, the organic phase was then washed with deionized water. The organic layer was separated from a turbid aqueous phase, dried over Na$_2$SO$_4$ and concentrated at 60° C. in vacuo to remove the solvent. Yield of the epoxy triglyceride was 558.4 g; the kinematic viscosities measured were: $\eta_{40°\,C.}$=164.4 cSt and $\eta_{100°\,C.}$=19.22 cSt, that is, a viscosity index of 133. PV=9.4, IV=1.79. Specific rotation $[\alpha]_D^{20}$=+0.17°. FT-IR (film on NaCl discs) cm$^{-1}$: 3471 w, 2927 vs, 2856 vs, 1743 vs, 1560 w, 1463 s, 1375 s, 1242 s, 1162 s, 1105 s, 1048 s, 845-824 d (m), 726 w-m. $^1$H-NMR (main fraction in CDCl$_3$) δ (ppm): 5.25 m (residual vinylic), 4.29 dd (J=4.3, 11.9 Hz, 2H), 4.14 dd (J=5.9, 11.9 Hz, 2H), 3.1 m (2H), 2.96 m (2H), 2.89 m (2H), 2.3 m (6H), 1.75-1.25 m (72H), 0.87 m (9H). $^{13}$C(CDCl$_3$) δ (ppm): 173.1, 172.7 (—C═O); 68.87 (—CHO— glyceride back bone); 62.02 (—CH$_2$O— glyceride back bone); 57.10, 57.05, 56.91, 56.85, 56.63, 56.55, 54.25, 54.09 (—C—O—C— epoxide); 34.06, 33.90 (α-CH$_2$—); 31.79, 31.61 (C11 of linoleyl moieties); 29.63, 29.47, 29.28, 29.23, 29.15, 29.12, 28.92, 28.88 (—CH$_2$-contiguous to hydroxylated carbons); 27.83, 27.77, 27.75, 27.16, 26.88, 26.55, 26.52, 26.08, 24.73 (—CH$_2$—); 22.51 (—CH$_2$— next to terminal —CH$_3$); 13.93 (terminal —CH$_3$).

Synthesis of Milkglyde: Amidohydroxy Gliadinyl Triglyceride of Milkweed Epoxide

In a semi-scaled up reaction milkweed epoxide (250.0 g, 262 mmol) was placed in a dry 1.0 L jacketed and fully baffled reactor into which were added dry powdered gliadin (110.0 g) and anhydrous ZnCl$_2$ (5.7 g). The reactor was equipped with an overhead stirrer and a heat regulator bath. The bath was connected and started and the temperature was set to 70° C. Meanwhile the reactor contents were gently purged with N$_2$ for 30 min after which the stirrer was started. Stirring was continued and occasionally adjusted until completion of reaction when the product solidifies into a rigid state. The heat source was turned off and the system allowed to cool to room temperature and the product reclaimed from the reactor by pulling it out. It had a slight tack and sheen which were removed with a quick acetone wash and drying in air to give 347.7 g (96.6%), an elastic solid. Its FT-IR spectrum on KBr disc is $v_{KBr}$ cm$^{-1}$: 3426 s (—N—H, O—H stretch), 2927 vs (—CH$_2$— asym stretch), 2855 s (—CH$_2$—, —CH$_3$ sym stretch), 1743 s (ester C═O), 1658 s (amide I), 1534 m (amide II), 1458 (—CH$_2$— deform), 1384 s (—CH$_3$ deform), 1244 (—OC—C-ester stretch), 1168 (—CHO—), 1095 (—C—CHO—), 723 (—CH$_2$— wag).

Example 2

Saliglyde

Synthesis of Salicornia Epoxy Triglyceride.

In a dry 1000 mL three-necked, round-bottomed jacketed flask equipped with an overhead stirrer and heated to 40° C., Salicornia oil (475.5 g, 583.65 mmol, iodine value=132.8) and 99% formic acid (49.56 g, 40.6 mL) were placed. The reaction mixture was vigorously stirred to homogeneity and hydrogen peroxide (50%, 274.87 g, 4.0416 mol, 232.9 mL) was added slowly. At the end of peroxide addition, the reaction temperature was raised to 70° C. while vigorous stirring was continued for 5 h when FT-IR spectrum of a reaction sample showed complete reaction. The heat source was turned off and the reaction was allowed to cool to room temperature. The contents of the reaction vessel were diluted with ethyl acetate (300 mL) and transferred into a separatory funnel. The separated aqueous layer was removed and the organic phase washed sequentially with brine (2×400 mL) followed with saturated Na$_2$CO$_3$ solution (50 mL) in additional saturated NaCl solution. The organic layer was then dried over Na$_2$SO$_4$ and concentrated under reduced pressure to give a colorless slightly viscous liquid (548.9 g). An overnight drying of the product at the pump yielded 512.9 g (98.9%) of the polyepoxy triglyceride. A transparent film of this product on NaCl discs showed the following FT-IR spectral bands, $v_{NaCl}$ cm$^{-1}$: 2927 vs (—CH$_2$— asym stretch) and 2856 s (—CH$_3$, —CH$_2$— sym), 1756 vs (O│C<ester), 1463 m-s (—CH$_2$— def), 1377 m (—CH$_3$ def), 1241 m-s (O═C—C), 1161 s (—CHO—), 1104 (—CHO—), 1048 (—CH$_2$O—), 844-825 d (—C—O—C— asym. epoxide stretch), 726 (—CH$_2$— wag). In contrast, the native oil gave IR bands that included 3019 cm$^{-1}$ w-m (H—C═C—) and 1654 vw (C═C breathing mode of the olefin. $^1$H NMR (CDCl$_3$) δ (ppm): 5.26 bs (1H), 4.31 d (J=11 Hz, 1H), 4.13 m (4H), 3.09 d (J=23 Hz, 4H), 2.93 d (J=38.2 Hz, 4H), 2.32 s (6H), 2.04 d (J=3.6 Hz, 2H), 1.8-1.2 m (69H), 0.90 bs (9H). $^{13}$C-NMR (CDCl$_3$) δ (ppm): 173.14, 172.74 (C═O); 68.90 (CHO glyceryl); 62.08, 60.34 (—CH$_2$O— glyceryl); 57.17, 57.11, 56.98, 56.91, 56.70, 56.62, 54.31, 54.15 (epoxy carbons); 34.12 (C-2), 33.95 (C-2), 31.65 (C-16), 29.67 (C-16), 29.64 (C-5), 29.52 (C-5), 29.33 (C-14), 29.29 (C-14), 29.25 (C-7), 29.16 (C-7), 28.97 (C-8), 27.89, 27.87, 27.82, 27.80, 27.21, 26.92, 26.59, 26.55, 26.44, 26.23, 26.12, 24.79 (C-3), 24.76 (—C-3), 22.55 (C-17); 14.18 (C-18), 13.96 (—C-18) ppm.

Synthesis of Saliglyde: Gliadinyl Amidohydroxy Triglyceride of Salicornia Epoxide In a typical reaction salicornia epoxide (250.0 g, 261.6 mmol) was placed in a dry 1.0 L jacketed and baffled 3-necked reactor equipped with an overhead stirrer. Dry powdered gliadin (100.0 g) together with anhydrous ZnCl$_2$ (4.6 g) were added. The heat regulator was started with a setting of 80° C. and the reactor contents were gently purged with N$_2$ (30 min). Thereafter the stirrer was started and the reaction mixture stirred to homogeneity. Stirring was continued and the reaction was monitored in five-h intervals by FT-IR until the epoxy C—O—C band at 845-824 cm$^{-1}$ disappeared or when the stirrer stops moving. The product was allowed to cool to near room temperature so it could be pulled out of the reactor and rinsed for two minutes with acetone and allowed to air-dry in the hood; yield was 355 g, >97%, an elastic solid. FT-IR spectrum $v_{KBr}$ cm$^{1}$: 3432 s (—N—H, —O—H stretch), 2928 vs (—CH$_2$— asym. stretch), 2856 s (—CH$_3$, —CH$_2$— sym. stretch), 1743 vs (>C═O ester), 1655 s (amide I), 1533 (amide II), 1465 (—CH$_2$— def), 1384 s (—CH$_3$ def), 1272 (O═C—C), 1166 (O—C—C—), 1075 (—CHO), 723 (—CH$_2$— wag).

Example 3

Soyglyde

Synthesis of Epoxy Soybean Triglyceride

In a dry 1000 mL three-necked jacketed reactor kettle equipped with an overhead stirrer, and an addition funnel and heated to 40° C., was added soybean oil (432.8 g, 0.494 mol). The oil was stirred vigorously and formic acid (99%, 34.12 g, 0.3 equiv) was added in one portion. This was followed by dropwise addition of 50% H$_2$O$_2$ (336 g, 9.88 mol). At the end of H$_2$O$_2$ addition the reaction temperature was raised to 70° C. and the reaction progress was monitored at 30 min. intervals by FT-IR spectrometry. At the end of 2 h, an FT-IR spectrum of a reaction sample showed complete disappearance of the 3010 cm$^{-1}$ band of the starting olefin in the reaction product, the heat was turned off and the system allowed to cool to room temperature as stirring continued. The product mixture was diluted with ethyl acetate and poured into a stirring solution of saturated NaCl/Na$_2$CO$_3$. After effervescence had subsided, the organic phase was separated and the aqueous layer extracted with more EtAc (200 mL×3). The combined organic phase was dried over Na$_2$SO$_4$ and concentrated under reduced pressure at 57° C. to give a quantitative yield, 492.7 g. FT-IR spectrum (film on NaCl discs) v cm$^{-1}$: 2927 vs, 2855 s, 1741 vs, 1461 m-s, 1381 m, 1241 m, 1161 s, 1101 m, 1021 w, 844-824 d, 722 m.

Synthesis of Amidohydroxy Gliadinyl Triglyceride (Soyglyde)

To 250 g, 262 mmol of epoxysoybean oil in a 1 L 3-necked, jacketed reaction kettle at 70° C. was added powdered gliadin (110.0 g), with 5.0 g of anhydrous $ZnCl_2$. The set-up was purged with $N_2$ for 15 min before the mixture was vigorously stirred. The reaction was monitored every three h by FT-IR spectroscopy for the disappearance of the stretching doublet of the epoxy moiety at 824-840 cm$^{-1}$. Because this band diminished very slowly two more aliquots of gliadin (25.0 g then 30.0 g) were added successively to the reaction until the epoxy bands were consumed or nearly so. Thus 262 mmol of epoxysoybean oil required 165.0 g of gliadin and 10.0 g of $ZnCl_2$ for complete reaction to produce 387.8 g of the soy oil amidohydroxy gliadinyl triglyceride or Soyglyde. Its FT-IR $v_{KBr}$ cm$^{-1}$: 3411 (N—H, OH), 2956 sh ($CH_3$ asym str.), 2930 vs ($CH_2$ sym. str), 2855 s ($CH_2$ asym str.), 1743 vs (C=O ester), 1657 vs (amide I, HN—C=O), 1535 m (amide II), 1454 m ($CH_2$ deform), 1383 s ($CH_3$ deform), 1239 m (OC—O—C), 1160 s (CHO stretch), 1060 m-s (NH, HCOH), 722 w ($CH_2$ wag).

Example 4

Thermal Analysis and Differential Scanning Calorimetry

Figure 6:
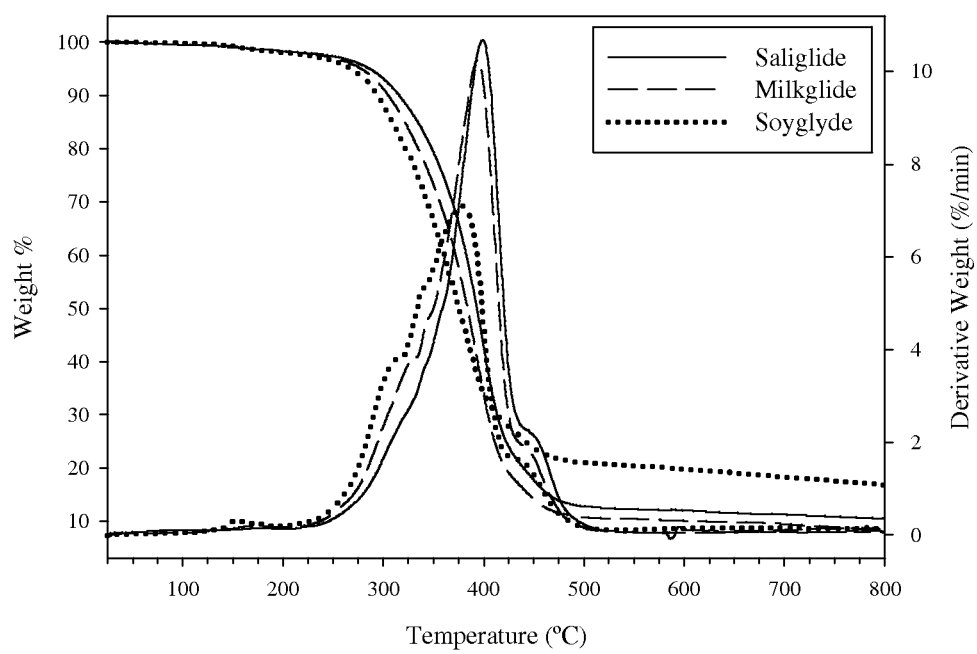
FIG. 6 is a graphical depiction of a TGA ("thermogravimetric analysis") scan of the reaction products of epoxidized salicornia oil with gliadin (saliglyde), epoxidized milkweed oil with gliadin (milkglyde), and epoxidized soybean oil with gliadin (soyglyde) in a nitrogen environment.
Figure 7:
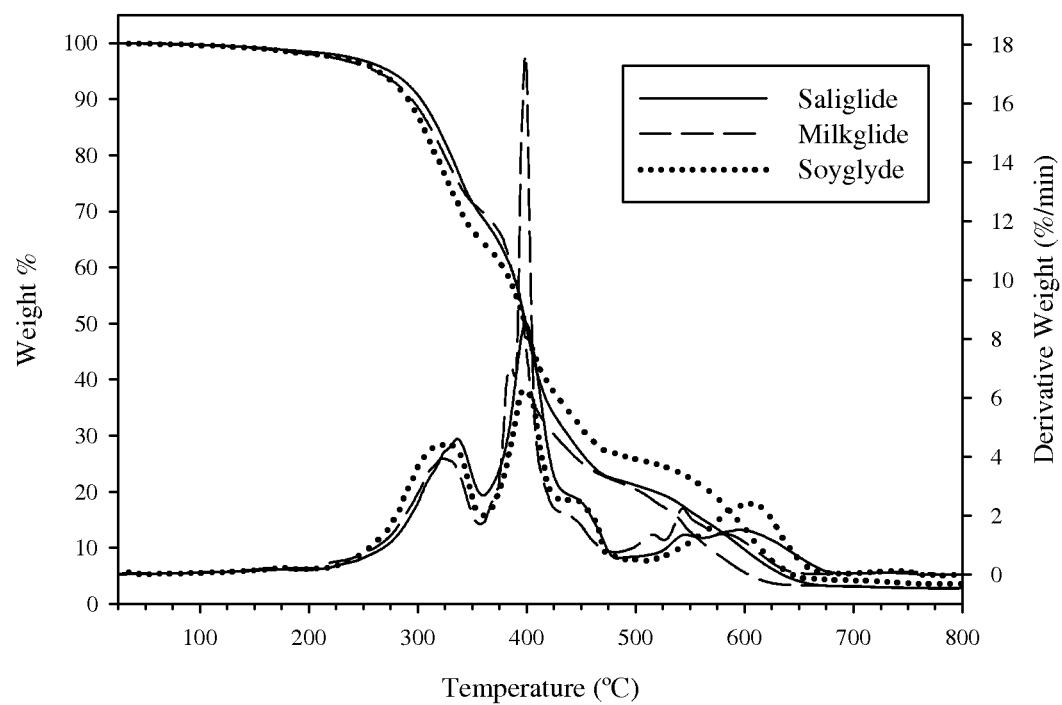
FIG. 7 is a graphical depiction of a TGA ("thermogravimetric analysis") scan of the reaction products of epoxidized salicornia oil with gliadin (saliglyde), epoxidized milkweed oil with gliadin (milkglyde), and epoxidized soybean oil with gliadin (soyglyde) in an atmospheric environment.

Thermogravimetric Analysis was performed on saliglyde, milkglyde, and soyglyde as follows. A sample (32-35 mg) was placed on an open platinum TGA pan and loaded on the TGA. The sample was heated in a nitrogen atmosphere at 10° C./min to 800° C. The derivative TGA of the sample showed initial degradation between 150 and 200° C., with the main degradation peaking at 399.6° C. and a smaller peak at 449.7° C. The compound showed 14% undegraded residue at 800° C., as shown in FIG. 6. The derivative of the TGA spectrum of saliglyde sample in nitrogen showed initial degradation between 150 and 200° C., with the main degradation peaking at 399.6° C. and a smaller peak at 449.7° C., FIG. 6. The compounds showed 14% undegraded residue at 800° C. in nitrogen, while in air 5.3% remained undegraded in air, FIG. 7.

Additionally, samples (23-25 mg) were sealed hermetically in a stainless steel DSC pan and tested using modulated DSC; heating rate 5±1° C./min to view the reversing and non-reversing heat flow results separately. The initial sample was cooled to −88° C. at a rate of 5° C./min and subsequently heated at the same rate (with modulation) to 150° C. This method was repeated for a second cycle. To eliminate the thermal history of the material a second sample was heated first from room temperature to 150° C., then cooled to −88° C. and heated again (all at 5° C./min). From the TGA data it was established that the compound started degrading around 200° C. instead of 150° C. So instead of 150° C., a new sample was heated to 200° C. right around the start of degradation. The material exhibited an exothermic transition at 168.5° C.

For soyglyde, the same sample size (23-25 mg) was hermetically sealed in a stainless steel DSC pan. The sample was run using modulated DSC (+/−1° C. every 60 sec) to view the reversing and non-reversing heat flow results separately. The initial sample was cooled to −88° C. at a rate of 5° C./min, and then heated at the same rate (with modulation) to 150° C. This method was repeated for a second cycle; however, there was no change in the results. A second sample was heated first to 150° C. from room temperature, then cooled to −88° C. and heated again (all at 5° C./min). Again, the results remained the same. This second sample was also heated to 200° C. on the second cycle to see if there were any differences. The only difference after heating to 200° C. was a slight exothermic peak, which is most likely the beginning stages of decomposition. (After the run, the pan was opened, and the sample showed some browning, which corresponds to degradation.)

The DSC results showed a possible glass transition between −50 and 0° C., with a possible 2-part transition. The peaks of the transition were at −27 and −7.8° C. Analyzed as 2 separate glass transitions, the results are shown in Table 1. It is clear from the table that, the second glass transition of soyglyde was observed above zero at 127.0° C., which is different from saliglyde and milkglyde, where both glass transitions appeared below zero.

Table 1. Temperatures of the Two Glass Transitions Observed in Saliglyde, Milkglyde and Soyglyde Sample DSC Thermogram

| Transition | Onset T (° C.) | Middle T (° C.) | End T (° C.) | ΔCp (J/g ° C.) |
|---|---|---|---|---|
| Saliglyde Tg #1 | −42.8 | −37.0 | −31.1 | 0.276 |
| Saliglyde Tg #2 | −18.7 | −16.2 | −13.6 | 0.133 |
| Milkglyde Tg #1 | −43.8 | −37.9 | −32.1 | 0.213 |
| Milkglyde Tg #2 | −19.4 | −16.6 | −13.8 | 0.0854 |
| Soyglyde #1 | −56.9 | −51.9 | −47.2 | 0.376 |
| Soyglyde #2 | 118.9 | 127.0 | 135.1 | 0.239 |

The effect of drying method on the thermal properties of the composite was done by heat drying and low relative humidity. Samples of soyglyde were also dried using Thermogravimetric Analysis (TGA) and Dynamic Vapor Sorption (DVS), with similar results. The TGA-dried sample (dried at 110° C. for 3 hrs in nitrogen) showed a very similar DSC profile, while the DVS-dried sample (dried at 85° C. and 0% humidity for 2 days) showed a 2-3° C. shift in the peak temperature of the two peaks (from −27 and −7.8° C., to −23.8 and −5.5° C.). The glass transition temperatures also shifted; however, the ΔCp were similar.

Rheological Measurements

Linear viscoelastic measurements were conducted for the composites. To ensure that all the measurements for the materials were made within the linear viscoelastic range, a strain-sweep experiment was conducted initially. An applied shear strain value in the linear range was adopted for the other viscoelastic property measurements for the same material; new samples were used for each experiment. 0.1% shear strain was used for the measurements of all three composites. Linear viscoelasticity indicates that the measured parameters are independent of applied shear strain. Small-amplitude oscillatory shear strain experiments were conducted over a frequency (w) range of 0.1-500 rad/s, yielding the storage or elastic (G') moduli and loss (G") moduli. The storage modulus represents the non-dissipative component of mechanical properties. The elastic or "rubber-like" behavior is suggested if the G' spectrum is independent of frequency and greater than the loss modulus over a certain range of frequency. The loss modulus represents the dissipative component of the mechanical properties and is characteristic of viscous flow. The phase shift or phase angle (δ) is defined by $\delta = \tan^{-1}(G''/G')$, and indicates whether a material is solid with perfect elasticity (δ=0), or fluid with pure viscosity (δ=90°), or something in between. Stress relaxation measurements were also performed in the linear viscoelastic range. Stress relaxation experiments measured the stress relaxation with time after the material is subject to a step increase in shear strain.

Figure 8:
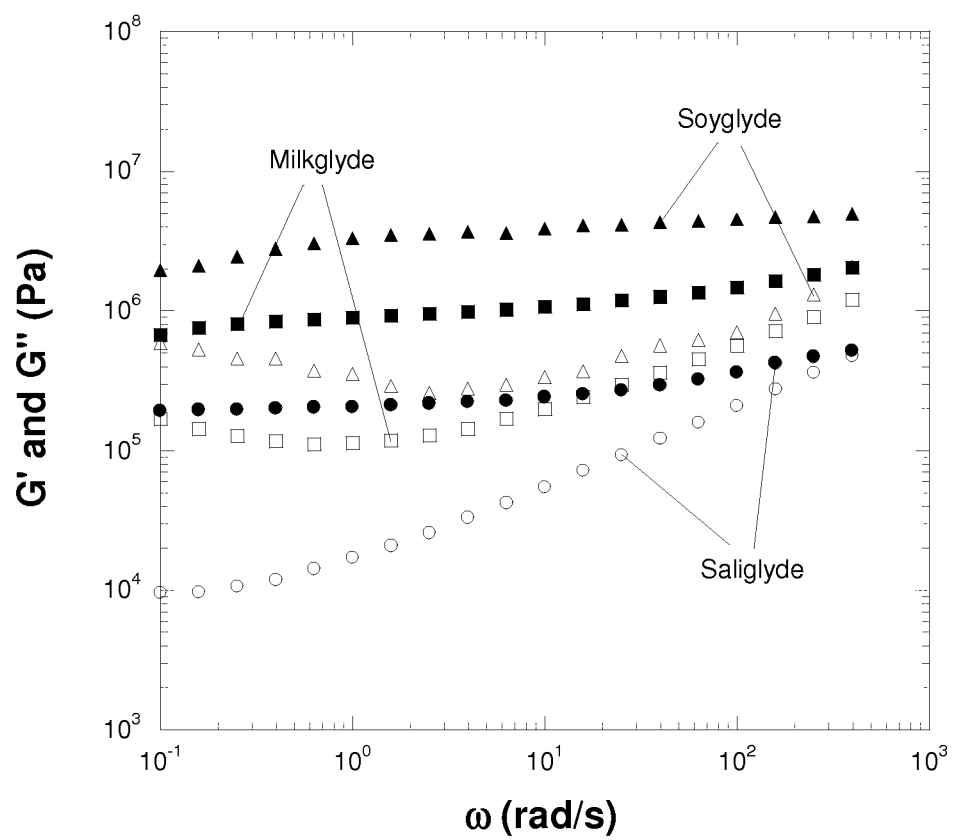
FIG. 8 is a graph depicting the storage modulus (G') and loss modulus (G") of the reaction products of epoxidized salicornia oil with gliadin (saliglyde), epoxidized milkweed oil with gliadin (milkglyde), and epoxidized soybean oil with gliadin (soyglyde) at 25° C. with 0.1% strain, wherein the solid symbols depict G' and the open symbols depict G".
Figure 9:
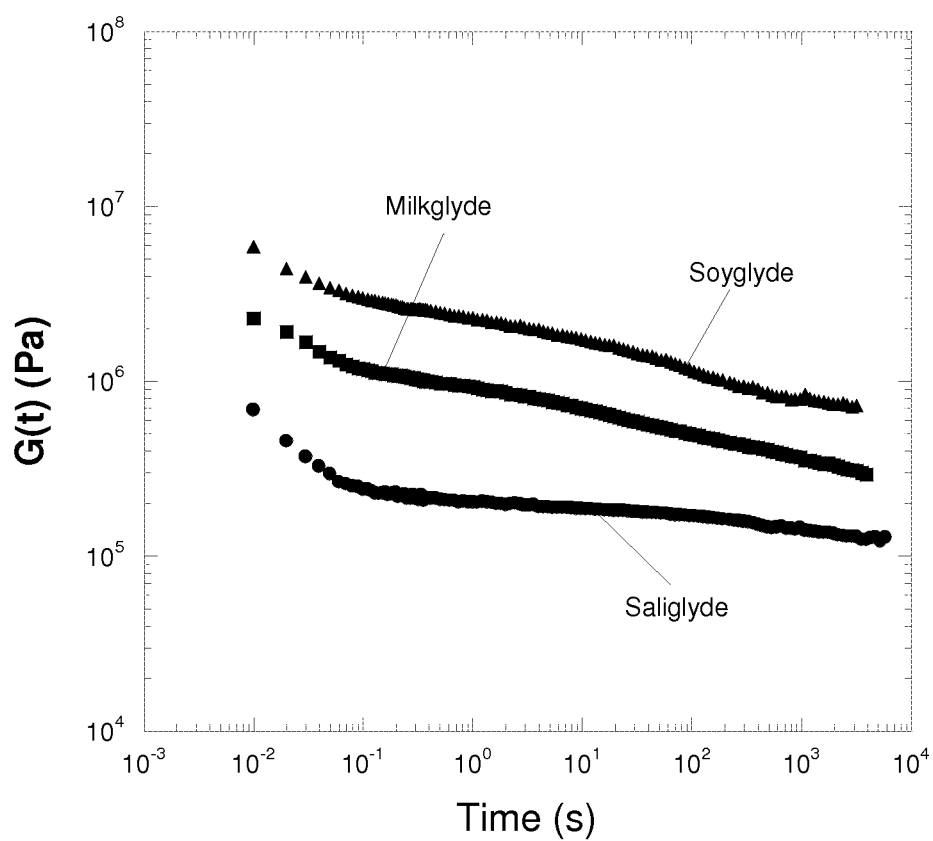
FIG. 9 is a graphical depiction of the stress relaxation exhibited by the reaction products of epoxidized salicornia oil with gliadin (saliglyde), epoxidized milkweed oil with gliadin (milkglyde), and epoxidized soybean oil with gliadin (soyglyde) as measured with a strain-controlled Rheometric ARES rheometer device.

All three composites of saliglyde, milkglyde and soyglyde exhibited viscoelastic solid behavior. The storage moduli (G') were greater than the loss moduli (G") at all measured frequencies (FIG. 8). FIG. 8. displays the linear viscoelastic properties of the composites at 25° C. Among the three composites, soyglyde showed the strongest viscoelastic solid properties, while saliglyde exhibited the weakest (FIG. 8). The storage moduli (G') for all three composites were almost independent of the frequency; and the curve had a plateau over the three frequency decades, which was similar to that for rubber (Ferry, J. D., 1980, Viscoelastic Properties of Polymers, $3^{rd}$ ed., Wiley, New York). Their loss moduli (G") curves were lower than those of G' at all measured frequencies, but were relatively more frequency dependent, especially for the composite saliglyde (FIG. 8). The elastic or storage moduli (G') at 1 rad/s were about $3.3 \times 10^6$, $9.0 \times 10^5$, and $2.1 \times 10^5$ for the soyglyde, milkglyde, and saliglyde respectively. The phase shifts ($\delta$) were in the range of 4.2°-22.7°, 7.2°-30.5°, and 2.9°-42.8° for the soyglyde, milkglyde, and saliglyde respectively. The shape of the G' curve for the milkglyde composite was also very similar to that of rubber (Id.) In the preparation of soyglyde, the soyepoxide required a greater amount of gliadin reagent for reaction completion than was needed in the epoxy milkweed reaction. This reflects the higher level of unsaturation and therefore a greater cross-linker capacity in soybean oil than its milkweed counterpart. Thus, soyglyde exhibited the strongest viscoelastic solid behavior among the three composites. And it is also reasonable that milkglyde showed stronger viscoelastic properties than saliglyde since milkweed oil had more cross-linking capacity than salicornia oil. Thus, the cross-linking capacity controlled the rheological properties of the three composites. For reference, a lightly cross-linked polymer, Hevea rubber exhibits elastic modulus about $7 \times 10^5$ Pa at 25° C. (Id.); and some synthetic elastomers, such as styrene-butadiene rubber and chloroprene rubber, display elastic moduli in the range of $1 \times 10^6$ to $3 \times 10^6$ Pa (Brostow, W., et al., 1996, Mechanical Properties, in Physical Properties of Polymers Handbook, pp 313-334). Therefore, the elasticity of all three composites were very close to those for some natural and synthetic rubbers. Stress relaxation experiments for the composite were also conducted (FIG. 9). The relaxation spectrum indicated that all three composites only relaxed very little after more than 2000 seconds (FIG. 9). If a network is not cross-linked or not tightly entangled, the network should quickly relax, and relaxation time should be very short. If a network is tightly cross-linked chemically, there should be no relaxation, and the relaxation time should be infinite. While a rubber-like material is held at an initial deformation, which is how the relaxation measurement is conducted, the stress and relaxation modulus (G(t)) will slowly decrease with time as the cross-linked network approaches an equilibrium condition. The relaxation measurements for the composites soyglyde, milkglyde, and saliglyde showed that they had similar relaxation behaviors as lightly cross-linked rubbers. Overall, the viscoelastic properties studies for these three composites suggested that they have similar viscoelastic properties as some natural and synthetic elastomers. And their viscoelastic behaviors can be controlled by the amount of cross-linking. Thus, there should be a high potential to use composites soyglyde, milkglyde, and saliglyde in replacement of some of the synthetic rubbers.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. An elastomer composition comprising the reaction product of: (A) an epoxidized vegetable oil triglyceride having 3 to 5 oxirane moieties per triglyceride unit substituted with (B) gliadin, said gliadin having one or more of the glutamine or arginine moieties, wherein the reaction product forms an elastomer.

2. The elastomer composition of claim 1 wherein the epoxidized vegetable oil triglyceride is epoxidized soybean oil.

3. The elastomer composition of claim 1 wherein the epoxidized vegetable oil triglyceride is epoxidized milkweed oil.

4. The elastomer composition of claim 1 wherein the epoxidized vegetable oil triglyceride is epoxidized salicornia oil.

5. A method for making an elastomer from a vegetable oil, the method comprising:

(A) epoxidizing a vegetable oil with a peroxide to form an epoxidized vegetable oil, (B) reacting said epoxidized vegetable oil having at least 3 oxirane moieties with gliadin, said gliadin having one or more glutamine or arginine moieties found in gliadin, wherein an elastomer product is formed.

6. The method of claim 5, wherein the vegetable oil is salicornia oil.

7. The product produced by the method of claim 6.

8. The method of claim 5, wherein the vegetable oil is milkweeds oil.

9. The product produced by the method of claim 8.

10. The method of claim 5, wherein the vegetable oil is soybean oil.

11. The product produced by the method of claim 10.

* * * * *

SEQUENCE LISTING

<160> NUMBER OF SEQ ID NOS: 2

<210> SEQ ID NO 1
<211> LENGTH: 262
<212> TYPE: PRT
<213> ORGANISM: Triticuim spp.

<400> SEQUENCE: 1

```
Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Pro Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Leu Gln Pro Gln Leu Pro Tyr Ser Gln Pro Gln Pro Phe Arg Pro
            85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Gln Ile Ile Gln Gln Ile Leu Gln Gln Gln Leu
    130                 135                 140
```

```
Ile Pro Cys Met Asp Val Val Leu Gln Gln His Asn Ile Val His Gly
145                 150                 155                 160

Lys Ser Gln Val Leu Gln Gln Ser Thr Tyr Gln Leu Leu Gln Glu Leu
                165                 170                 175

Cys Cys Gln His Leu Trp Gln Ile Pro Glu Gln Ser Gln Cys Gln Ala
            180                 185                 190

Ile His Asn Val Val His Ala Ile Ile Leu His Gln Gln Gln Lys Gln
        195                 200                 205

Gln Gln Gln Pro Ser Ser Gln Val Ser Phe Gln Gln Pro Leu Gln Gln
    210                 215                 220

Tyr Pro Leu Gly Gln Gly Ser Phe Arg Pro Ser Gln Gln Asn Pro Gln
225                 230                 235                 240

Ala Gln Gly Ser Val Gln Pro Gln Gln Leu Pro Gln Phe Glu Glu Ile
                245                 250                 255

Arg Asn Leu Ala Arg Lys
                260

<210> SEQ ID NO 2
<211> LENGTH: 12
<212> TYPE: PRT
<213> ORGANISM: Triticuim spp.

<400> SEQUENCE: 2

Arg Pro Gln Gln Pro Tyr Pro Gln Pro Gln Pro Gln
1               5                   10
```